United States Patent [19]

Richard et al.

[11] Patent Number: 5,962,484

[45] Date of Patent: Oct. 5, 1999

[54] PHOTOPROTECTIVE/COSMETIC COMPOSITIONS COMPRISING SUBSTITUTED POLYORGANOSILOXANES/ POLYORGANOSILANES

[75] Inventors: Hervé Richard, Villepinte; Madeleine Leduc, Paris; Alain Lagrange, Coupvray, all of France

[73] Assignee: Societe L'Oreal S.A., Paris, France

[21] Appl. No.: 08/832,678

[22] Filed: Apr. 9, 1997

Related U.S. Application Data

[62] Division of application No. 08/541,983, Oct. 10, 1995, Pat. No. 5,663,270.

[30] Foreign Application Priority Data

Oct. 7, 1994 [FR] France ................................ 94 12004

[51] Int. Cl.$^6$ ................................ A01N 25/02; A61K 7/42
[52] U.S. Cl. ..................... 514/359; 548/257; 548/259; 548/260; 548/110; 424/59; 424/70.9; 424/401; 528/15; 528/27; 528/31
[58] Field of Search ................... 548/257, 259, 548/260, 110; 424/401, 59, 70.9; 514/359; 528/15, 27, 31

[56] References Cited

U.S. PATENT DOCUMENTS

| | | | |
|---|---|---|---|
| 3,936,418 | 2/1976 | Pond et al. | 260/45.8 |
| 5,089,250 | 2/1992 | Forestier et al. | 424/43 |
| 5,254,542 | 10/1993 | Sakuta et al. | 514/63 |

OTHER PUBLICATIONS

Chemical Abstracts 11539e, "2–(2–Hydroxy–3–Alkenyl–5–Methylphenyl)Benzotriazoles", Apr. 1963.

*Primary Examiner*—Frederick Krass
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise a photoprotecting effective amount of a novel benzotriazole-substituted polyorganosiloxane/polyorganosilane having one of the formulae (1) to (3):

$$B-\underset{\underset{R}{|}}{\overset{\overset{R}{|}}{Si}}-O-\left[\underset{\underset{R}{|}}{\overset{\overset{R}{|}}{Si}}-O\right]_r-\left[\underset{\underset{A}{|}}{\overset{\overset{R}{|}}{Si}}-O\right]_s-\underset{\underset{R}{|}}{\overset{\overset{R}{|}}{Si}}-B \quad (1)$$

$$\left[\left[\underset{\underset{R}{|}}{\overset{\overset{R}{|}}{Si}}-O\right]_t\left[\underset{\underset{A}{|}}{\overset{\overset{R}{|}}{Si}}-O\right]_u\right] \quad (2)$$

$$A-Si(R')_3 \quad (3)$$

wherein A is a monovalent benzotriazole radical bonded directly to a silicon atom and having the formula (4):

$$\left[\begin{array}{c}\text{benzotriazole-phenol structure}\end{array}\right]\begin{array}{l}-(Y)_n\\-(X)_m-(CH_2)_p-\underset{\underset{Z}{|}}{CH}-CH_2-;\end{array} \quad (4)$$

the compounds of formulae (1) to (3) are prepared, e.g., via hydrosilylation, from novel intermedates, per se also exhibiting sunscreen activity, and having the formula (4a):

$$\left[\begin{array}{c}\text{benzotriazole-phenol structure}\end{array}\right]\begin{array}{l}-(Y)_n\\-(X)_m-(CH_2)_p-\underset{\underset{Z}{|}}{C}=CH_2.\end{array} \quad (4a)$$

6 Claims, No Drawings

PHOTOPROTECTIVE/COSMETIC COMPOSITIONS COMPRISING SUBSTITUTED POLYORGANOSILOXANES/ POLYORGANOSILANES

This application is a divisional of application Ser. No. 08/541,983, filed Oct. 10, 1995, now U.S. Pat. No. 5,663,270.

BACKGROUND OF THE INVENTION

1. Technical Field of the Invention

The present invention relates to novel compounds comprising short-chain, linear or cyclic diorganosiloxanes or triorganosiloxanes bearing at least one alkoxybenzotriazole substituent.

The present invention also relates to novel cosmetic compositions for topical application comprising said substituted polyorganosiloxanes, for the photoprotection of the skin and/or the hair against ultraviolet radiation.

This invention also relates to novel ethylenically unsaturated alkoxybenzotriazoles that are useful intermediates for the synthesis of the aforesaid substituted polyorganosiloxanes.

2. Description of the Prior Art

It is known to this art that light radiation of wavelengths of from 280 nm to 400 nm promotes tanning of the human epidermis, and that irradiation of wavelengths of from 280 to 320 nm, i.e, UV-B irradiation, causes erythema and skin burns which can impair the development of a natural tan; hence, such UV-B radiation must thus be screened from the skin.

It is also known to this art that UV-A radiation, of wavelengths of from 320 to 400 nm, which tans the skin, also adversely affects it, in particular in the event of sensitive skin or skin constantly exposed to solar radiation. UV-A irradiation causes, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of compounds intended for the photoprotection (UV-A and/or UV-B) of human skin are known to this art.

Most of these are aromatic compounds displaying an absorption of UV radiation in the region from 280 to 315 nm or in the region of from 315 to 400 nm, or else in both of these regions together. They are, more often than not, formulated in sunscreen compositions as oil-in-water emulsions (namely, a cosmetically acceptable vehicle, carrier or diluent comprising an aqueous continuous dispersing phase and an oily discontinuous dispersed phase) which contain, at various concentrations, one or more traditional lipophilic and/or hydrophilic organic sunscreen compounds comprising an aromatic function suitable for selectively absorbing harmful or deleterious UV radiation. These sunscreen compounds (and the amounts thereof) are selected as a function of the desired specific sun protection factor (the specific protection factor (SPF) being expressed mathematically by the ratio of the irradiation time required to attain the erythemogenic threshold with the UV screening agent to the time required to attain the erythemogenic threshold in the absence of UV screening agent.)

Other than their sunscreen activity, these compounds having anti-UV properties must also display good cosmetic characteristics in the compositions comprised thereof, good solubility in common solvents, and especially fats such as oils and greases, and also good resistance to water and to perspiration (durability).

Among such prior art aromatic compounds, p-aminobenzoic acid derivatives, benzylidenecamphor derivatives, cinnamic acid derivatives and benzotriazole derivatives are particularly representative. However, certain of these compounds do not display all of the properties required for an acceptable UV screening agent in sunscreen compositions. In particular, their intrinsic screening activity may be insufficient, their solubility in the different formulations employed for photoprotection is not always sufficiently good (fat solubility in particular), they may not possess sufficient stability to light (photostability) and they may also display resistance to water and to sweat. It is also desirable that these sunscreen compositions do not penetrate the skin.

Thus, in the particular case of sunscreen compounds of the benzotriazole type, derivatives thereof have been prepared which have improved properties, especially in respect of their fat solubility and their cosmetic character, by effecting bonding of the benzotriazole screening group via grafting (hydrosilylation) onto a macromolecular chain of the silicone (organopolysiloxane) type. Such derivatives are described in EP-0,392,883, assigned to the assignee hereof, and are generally denominated "silicone screening agents", but the fat-solubility of these compounds can still be inadequate and, furthermore, in order to provide satisfactory sunscreen properties, it is often necessary to employ relatively large amounts of these photoprotective polymers, resulting in poor cosmetic properties in respect of the formulations comprised thereof.

SUMMARY OF THE INVENTION

Accordingly, a major object of the present invention is the provision of novel benzotriazole-substituted silicone/silane sunscreen compounds, which display improved properties, in particular in respect of their solubility in fats, their cosmetic properties and their intrinsic absorbing activity with respect to UV irradiation.

Thus, it has now unexpectedly been determined that by bonding, in particular via hydrosilylation, one or more specific benzotriazole derivatives, namely, more especially, alkoxybenzotriazoles, to a particular linear or cyclic silicone chain or a particular silane, novel silicone sunscreen compounds are prepared which avoid or conspicuously ameliorate the above disadvantages and drawbacks of the prior art silicone sunscreens, said novel compounds displaying, in particular, very high sunscreen activity, very good solubility in common organic solvents, and notably fats such as oils, and also excellent cosmetic properties. These novel silicone sunscreen compounds are very well suited for formulation into photoprotective/cosmetic compositions for protecting the skin and/or hair against the damaging effects of ultraviolet radiation.

Briefly, the present invention features novel compounds having one of the following formulae (1) to (3):

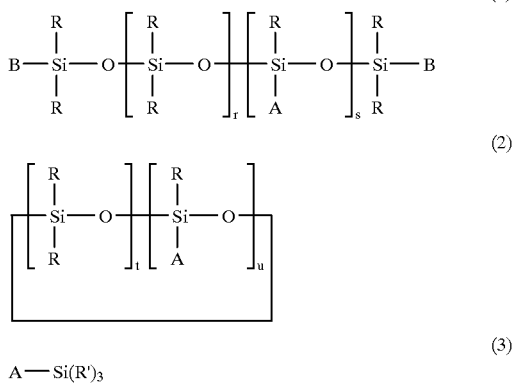

(1)

(2)

(3)

in which the radicals R, which may be identical or different, are each $C_1$–$C_{10}$ alkyl, phenyl or 3,3,3-trifluoropropyl radicals, at least 80% by number of the radicals R being methyl radicals; the radicals B, which may be identical or different, are each a radical R or a radical A as defined below; the radicals R', which may be identical or different, are each a $C_1$–$C_8$ alkyl radical or a phenyl radical; r is an integer ranging from 0 to 50, inclusive, and s is an integer ranging from 0 to 20, inclusive, with the proviso that, if s is zero, then at least one of the two radicals B is a radical A; u is an integer ranging from 1 to 6, inclusive, and t is in integer ranging from 0 to 10 inclusive, with the proviso that t+u is equal to or greater than 3; and the radical A is a univalent radical bonded directed to a silicon atom, and which has the following formula (4):

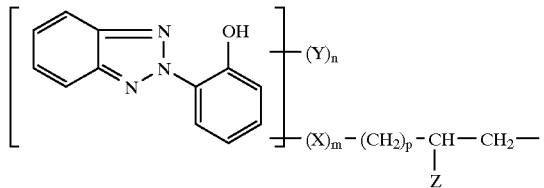

(4)

wherein the radicals Y, which may be identical or different, are each a $C_1$–$C_8$ alkyl radical, a halogen atom or a $C_1$–$C_4$ alkoxy radical, with the proviso that, in the latter event, two adjacent radicals Y on the same aromatic nucleus can together form an alkylidenedioxy radical in which the alkylidene group has from 1 to 2 carbons atoms; X is O or NH; Z is hydrogen or a $C_1$–$C_4$ alkyl radical; n is an integer ranging from 0 to 3, inclusive; m is 0 or 1, with the proviso that, when m is zero, or when m is equal to 1 and X is NH, necessarily (i) n cannot be zero and (ii) at least one of the radicals Y is an alkoxy radical; and p is an integer ranging from 1 to 10, inclusive.

DETAILED DESCRIPTION OF BEST MODE AND PREFERRED EMBODIMENTS OF THE INVENTION

More particularly according to the present invention, in the above formulae (1) to (3), A is thus the radical derived from the benzotriazole which, after bonding to the starting short silicone chain or to the starting silane, imparts to the compounds of the linear diorganosiloxane type (formula (1)), or of the cyclic diorganosiloxane type (formula (2)), or of the triorganosiloxane type (formula (3)), with absorbing properties with respect to ultraviolet in a wavelength region which can range from 280 nm to 400 nm. As indicated above, and as is apparent from the definition of the above formula (4), this group necessarily comprises at least one alkoxy function bonded to at least one of the two aromatic rings of the benzotriazole, it being possible for this alkoxy function to be provided either by a substituent Y or by the linking moiety which couples the benzotriazole to the silicone chain or to the silane.

One of the great advantages presented by the compounds according to the invention is that, depending on the position occupied by this/these alkoxy group(s) on the sunscreen structural unit A, photoprotective agents are prepared which are either purely UV-A sunscreens, or, to the contrary, purely UV-B sunscreens, with extinction coefficients in all instances well above those characterizing the silicone sunscreen agents of the prior art. Thus, purely by way of example, derivatives substituted by an alkoxy group at the ortho-position with respect to the hydroxyl group borne by the benzene ring (position 3) provide silicone photoprotection agents predominantly adsorbing in the UV-B region, whereas derivatives substituted by an alkoxy group at the meta-position (i.e., positions 4 and/or 6) with respect to this same hydroxyl group provide silicone photoprotection agents predominantly absorbing in the UV-A region.

As is apparent from the above formula (4), the coupling of the linking radical —(X)$_m$—CH$_2$)$_p$—CH(Z)—CH$_2$— to the benzotriazole nucleus thus bonds the benzotriazole nucleus to a silicon atom of the silicone backbone or of the silane, and this substitution can be effected at all available positions afforded by the two aromatic rings of the benzotriazole:

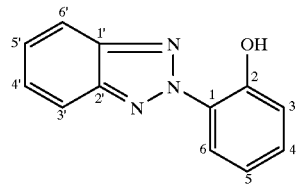

Preferably, this coupling is at position 3, 4, 5 (aromatic ring bearing the hydroxyl function) or 4' (benzene ring fused to the triazole ring), and even more preferably at position 3, 4 or 5.

Likewise, the coupling of the substituent Y can be at all other available positions of the benzotriazole. However, this coupling is preferably at positions 3, 4, 4', 5 and/or 6.

In the above formulae (1) to (3), the alkyl radicals can be linear or branched and are advantageously selected from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals R, R' and B according to the invention are methyl, ethyl, propyl, n-butyl, n-octyl and 2-ethylhexyl radicals. Even more preferably, the radical R, R' and B are all methyl radicals.

Among the compounds of the above formulae (1) to (3), preferred are those corresponding to the formula (1) or to the formula (2), namely, short-chain, linear or cyclic diorganosiloxanes.

Among the linear or cyclic diorganosiloxanes according to the present invention, preferred are the statistical or well-defined block-containing compounds having at least one, and even more preferably all, of the following definitions:

R is alkyl and even more preferably methyl,

B is alkyl and even more preferably methyl (applicable to the linear compounds of formula (1)), r ranges from 0 to 3, inclusive; s ranges from 0 to 3, inclusive (applicable to the linear compounds of formula (1)), t and u ranges from 3 to 5 (applicable to the cyclic compounds of formula (2)), n is not zero and is preferably equal to 1 or 2, and Y is then selected from among methyl, tert-butyl and $C_1$–$C_4$ alkoxy radicals, but preferably from among $C_1$–$C_4$ alkoxy radicals, and is even more preferably a methoxy radical, Z is hydrogen or methyl, X is 0 (m≠0), p is equal to 1, with the proviso that, in all instances, at least one alkoxy function is coupled directly to the benzotriazole compounds.

To prepare the silicone sunscreen agents of formulae (1) and (2), a traditional synthesis can be employed, i.e., a hydrosilylation reaction (namely,

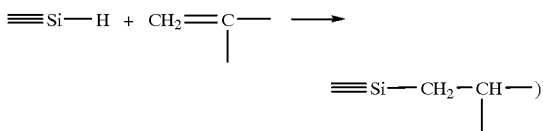

starting from the corresponding silicone in which, for example, all of the radicals A are hydrogen atoms. This starting silicone will hereinafter be designated the SiH-containing derivative; the SiH groups may be present in the silicone backbone and/or at the ends of the silicone chain. These SiH-containing derivatives are well known compounds in the silicone industry, and are generally commercially available. They are, for example, described in U.S. Pat. Nos. 3,220,972, 3,697,473 and 4,340,709.

This SiH-containing derivative may thus be represented either by the following formula (1a):

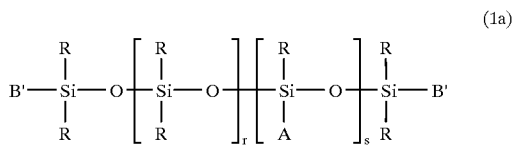

in which R, r and s are as defined above in respect of the formula (1) and the radicals B', which may be identical or different, are selected from among the radicals R and a hydrogen atom, or by the following formula (2a):

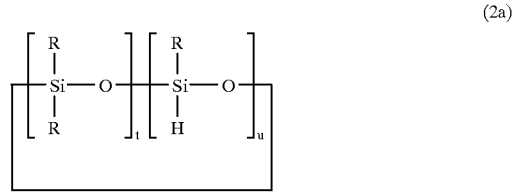

in which R, t and u are as defined above in respect of the formula (2).

This SiH-containing derivative of formulae (1a) or (2a) is reacted, via traditional hydrosilylation reaction, carried out in the presence of a catalytically effective amount of a platinum-based catalyst, with an organic benzotriazole compound having the following formula (4a):

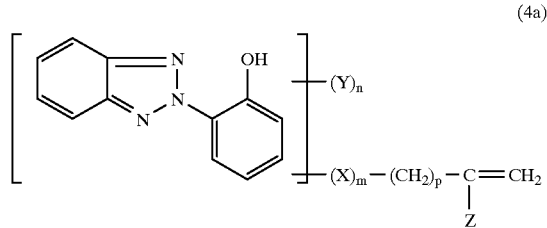

in which Y, X, Z, n, m and p are as defined above in respect of the formula (4).

Processes suitable for the preparation of the compounds of formula (4a) are described, in particular, in U.S. Pat. Nos. 4,316,033 and 4,328,346.

In addition, the working conditions to be observed for conducting the hydrosilylation reaction between the compounds of formula (1a) or (2a) above with the compound of formula (4a) above are reported in the aforesaid EP-O-392,883, hereby expressly incorporated by reference.

As regards the photoprotective agents of the triorganosilane type of formula (3), these can be prepared via hydrosilylation reaction between a starting silane of formula (R')$_3$SiH (formula (3a)), in which R' is as defined above in resect of the compounds of formula (3), and an organic benzotriazole derivative of above formula (4a).

As indicated above, the monoethylenically unsaturated organic benzotriazole compounds of formula (4a) are novel compounds useful, per se, as sunscreen agents in the UV-A and/or UV-B range, especially in cosmetic compositions intended for photoprotection of the skin or hair.

Relative to the silicone photoprotective agents of the prior art, as are described in EP-0,392,883, the silicone sunscreen agents according to the invention hence exhibit one or several essential structural differences which are the source of their exceptional properties: the silicone chains onto which the benzotriazole structural unit is grafter are, on the one hand, much shorter, and, on the other, the structural unit derived from benzotriazole always bears at least one alkoxy substituent.

Also as indicated above, the compounds of formulae (1) to (3) above display excellent intrinsic screening activity with respect to ultraviolet radiation (UV-A and/or UV-B, depending on the structure of the compound). By admixing compounds of different structure, namely, more specifically, by mixing compounds according to the invention displaying purely UV-A activity with products according to the invention displaying purely UV-B activity, it is thus possible to provide a composition which will display overall an exceptional sunscreen activity over the entire range of harmful UV (UV-A+UV-B), which is a considerable advantage. In addition, by virtue of their strongly fat-soluble character, the compounds of formulae (1) to (3) above may be used at high concentrations, thereby imparting to the final compositions very high specific protection factors; moreover, they distribute themselves uniformly in the traditional cosmetic vehicles comprising at least one fatty phase or a cosmetically acceptable organic solvent, and may thus be applied to the skin or hair to form an effective protective film. Lastly, their cosmetic properties are very good, namely, in particular, these products, relative to the silicone screening agents of the prior art, are less sticky and render the skin or hair softer.

Thus, the present invention also features cosmetic compositions comprising, in a cosmetically acceptable vehicle, carrier or diluent, preferably including at least one fatty phase or at least one organic solvent, an effective photoprotective amount of at least one compound of the above formulae (1) to (3).

The compounds of formulae (1) to (3) are advantageously present in proportions ranging from 0.1% to 20% by weight, and preferably from 0.5% to 10% by weight, relative to the total weight of the composition.

The cosmetic compositions of the invention may be used as protective compositions for the human epidermis or hair against ultraviolet rays, as sunscreen compositions or as makeup products.

These compositions may be in the form, in particular, of a lotion, thickened lotion gel, cream, ointment, milk, powder or solid stick, and be packaged, where appropriate, as an aerosol and thus be in the form of a mousse or spray.

They can contain the usual cosmetic adjuvants and additives, such as fats, organic solvents, silicones, thickeners, emollients, additional sunscreen agents, foam inhibitors, hydrating agents, perfumes, preservatives, surfactants, fillers, sequestering agents, anionic, cationic, nonionic or amphoteric polymers or mixtures thereof, propellants, alkalinizing or acidifying agents, colorants, pigments or nanopigments, especially those designed to provide an additional photoprotective effect by physically blocking the ultraviolet radiation, or any other ingredient customarily used in cosmetics, especially for the production of sunscreen compositions.

Exemplary of the organic solvents are the lower polyols and alcohols, such as ethanol, isopropanol, propylene, glycol, glycerol and sorbitol.

The fats can comprise an oil or wax or mixtures thereof, fatty acids, fatty acid esters, fatty alcohols, petroleum jelly, paraffin, lanolin, hydrogenated lanolin and acetylated lanolin. The oils may be selected from among animal, vegetable, mineral or synthetic oils, and in particular hydrogenated palm oil, hydrogenated castor oil, liquid petrolatum, paraffin oil, Purcellin oil, volatile or non-volatile silicone oils and isoparaffins.

When the cosmetic compositions according to the invention are used for protecting the human epidermis against the deleterious or damaging effects of UV irradiation or as sunscreen compositions, they are advantageously formulated as a suspension or dispersion in solvents or fats, or, alternatively, in the form of an emulsion (in particular of the O/W or W/O type, but preferably O/W) such as a cream or milk, or of a vesicular dispersion, or as an ointment, gel, solid stick or aerosol mousse. The emulsions can contain, in addition, anionic, nonionic, cationic or amphoteric surfactants.

When the compositions according to the invention are used for the photoprotection of the hair, they can be formulated as a shampoo, lotion, gel or rinse, to be applied before or after shampooing, before or after dyeing or bleaching, before, during or after permanent-waving or straightening, as a styling or treatment lotion or gel, blow-drying or setting lotion or gel, hair lacquer or composition for permanent-waving or straightening, dyeing or bleaching the hair.

When the cosmetic compositions according to the invention are used as a makeup product for the eyelashes, eyebrows, skin or hair, such as a cream for treating the epidermis, makeup foundation, lipstick, eyeshadow, blush, eyeliner, mascara or coloring gel, they can be formulated in solid or pasty, anhydrous or aqueous form, such as oil-in-water or water-in-oil emulsions, suspensions or, alternatively, gels.

The cosmetic treatment of the skin or hair to protect same against the deleterious effects of ultraviolet radiation, especially solar radiation, comprises applying to the skin or hair an effective amount of a sunscreen/cosmetic composition as described above, or of a compound of the above formulae (1), (2) or (3), or, alternatively, of a benzotriazole compound of formula (4a).

In order to further illustrate the present invention and the advantages thereof, the following specific examples are given, it being understood that same are intended only as illustrative and in nowise limitative.

EXAMPLE 1

This example illustrates the preparation of a compound according to the invention and having the formula:

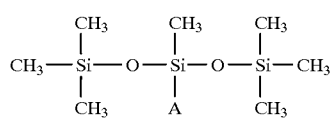

in which A is the radical:

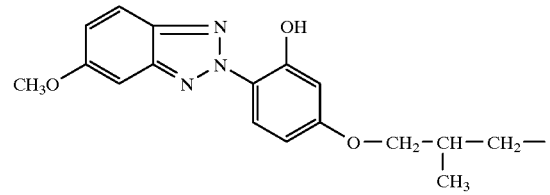

(this compound has formula (1) in which R=B=CH$_3$; r=0; s=1; Y=OCH$_3$, at position 4'; n=1; m=1 and X=0; p=1; Z=Ch$_3$).

(a) First stage:
Preparation of 4-(4-methoxy-2-nitrophenylazo)benzene-1,3-diol:

A solution of diazonium salt, obtained beforehand by diazotization of 67.2 g (equivalent to 0.4 mol) of 4-methoxy-2-nitroaniline contained in 150 ml of concentrated HCl with a sodium nitrite solution containing 28 g (equivalent to 0.4 mol) in 100 ml of water at 0°–5° C., was added at a temperature of between 5° and 10° C. and over one hour into a reactor containing 44 g (equivalent to 0.4 mol) of resorcinol dissolved in a mixture of 400 ml of ethanol and 400 ml of water. The mixture was maintained under stirring for 2 hours. The red precipitate was filtered off and then rinsed copiously with water. 86 g (yield: 74%) of the desired compound was thereby obtained.

(b) Second stage:
Preparation of 2-(4-methoxy-2-nitrophenylazo)-5-(2-methylallyloxy)phenol:

81 g (equivalent to 0.28 mol) of the compound obtained above, 220 ml of DMF and 42.6 g (equivalent to 0.308 mol) of potassium carbonate were introduced into a round-bottomed flask equipped with appropriate attachments. The mixture was heated to 80°–90° C., and 28 g (equivalent to 0.308 mol) of methallyl chloride were then introduced dropwise over 30 minutes. The mixture was then maintained under stirring at 90° C. for 4 h, 30 min. The reaction mixture was then poured into 200 g of ice-cold water and the precipitate obtained was filtered off. This precipitate was then taken up in dichloromethane, dried over sodium sulfate, concentrated and passed through a bed of silica 60. After evaporation of the solvent and drying, 47 g of a red powder (yield: 49%) consisting of the desired compound were obtained.

(c) Third stage:

Preparation of 2-(5-methoxy-2-benzotriazolyl)-5-(2-methylallyloxy)phenol:

32.54 g (equivalent to 0.134 mol) of the compound obtained above and 400 ml of ethanol were introduced into a round-bottomed flask. 48.4 g (equivalent to 0.269 mol) of glucose dissolved in 400 ml of 2N sodium hydroxide were added portionwise thereto over one-half hour, and the mixture was maintained under stirring overnight. 44.4 g of powered zinc were then added and the mixture was maintained under stirring for 3 hours. The mixture was then filtered and the residue was washed with dichloromethane. The filtrate was extracted with dichloromethane. The organic liquors were combined, washed with water and dried. After concentration and drying, 36.6 g of a grey-brown colored powder were obtained. It was recrystallized in ethanol, to thereby obtain 41.8 g (yield: 65%) of the desired compound having the formula:

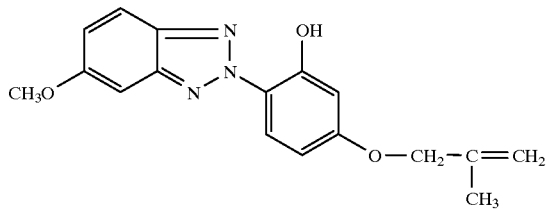

(d) Fourth stage:

Preparation of the desired final compound:

A reactor equipped with all appropriate attachments was charged with 21.8 g of the compound obtained above and 35 ml of toluene. The mixture was heated to 80° C. under nitrogen. The catalyst (complex containing 3%–3.5% by weight of Pt in cyclovinylmethylsiloxane marketed by Hüls, Petrarch PC085:100 µl) was added, and 16.5 g of heptamethyltrisiloxane were added dropwise over 5 minutes. The heterogeneous mixture was heated to reflux for 8 hours under nitrogen. The reaction medium was concentrated and chromatography was then performed on silica under pressure (eluent: heptane with a gradient of $CH_2Cl_2$). 25 g of a solid were then recovered, which was recrystallized in methanol to finally obtain 23.5 g (yield: 63%) of the desired final compound.

The UV absorption characteristics (measured in ethanol) of this compound were as follows:

$\lambda_{max}$: 349 nm $\epsilon_{max}$: 27,200

Hence, this compound is a very effective sunscreen agent which is active in the UV-A range.

EXAMPLE 2

Following the same procedure as in Example 1, (the only difference being that, in Stage 1, the 4-methoxy-2-nitroaniline had been replaced by 2-nitroaniline), 8.5 g (yield: 67%) were prepared of another compound according to the invention and having the following formula:

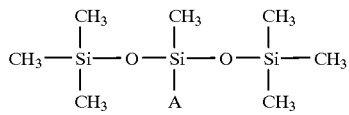

in which A was the radical:

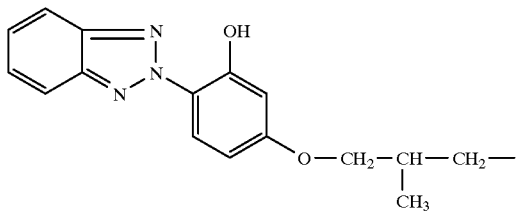

Hence, this compound differed from that of Example 1 only in the absence of the $OCH_3$ substituent on the benzotriazole nucleus.

The UV absorption characteristics (measured in ethanol) of this compound were as follows:

$\lambda_{max}$: 342 nm $\epsilon_{max}$: 24,500

Hence, this compound is a very effective sunscreen agent which is active in the UV-A range.

It should be appreciated that the intermediate compound obtained at the end of Stage 3 in the sequence of the process had the formula:

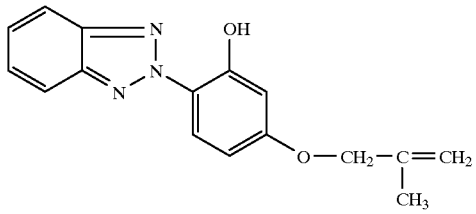

EXAMPLE 3

Following the same procedure as in Example 1, (the only difference being that, in Stage 1, the resorcinol was replaced by 4-methyl-2-(2-methylallyloxy)phenol, 2 g were prepared (yield: 54%) of another compound according to the invention and having the following formula:

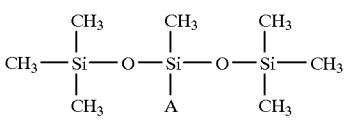

in which A was the radical:

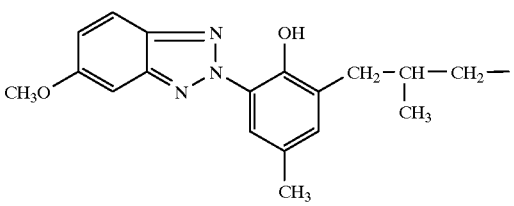

The UV absorption characteristics (measured in ethanol) of this compound were as follows:

$\lambda_{max}$: 303 nm $\epsilon_{max}$: 10,900

$\lambda_{max}$: 348 nm $\epsilon_{max}$: 22,200

Hence, this compound is a very effective sunscreen agent which is moderately active in the UV-B range and strongly active in the UV-A range.

It should be appreciated that the intermediate compound obtained at the end of Stage 3 in the sequence of the process had the formula:

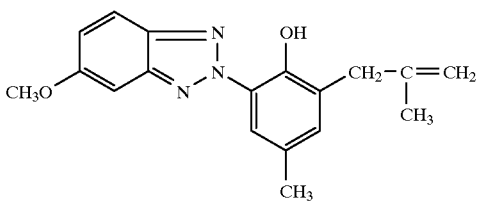

EXAMPLE 4

Following the same procedure as in Example 1 (the only differences being that, on the one hand, in Stage 1, the 4-methoxy-2-nitroaniline and resorcinol were replaced by 2-nitroaniline and eugenol, respectively, and that, on the other, Stage 2 was eliminated), 13 g (yield: 67%) were prepared of another compound according to the invention and having the following formula:

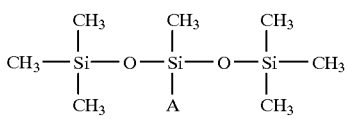

in which A was the radical:

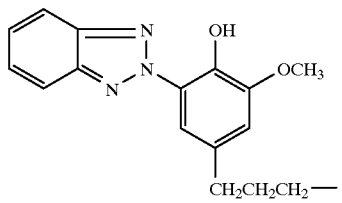

The UV absorption characteristics (measured in ethanol) of this compound were as follows:

$\lambda_{max}$: 310 nm $\epsilon_{max}$: 17,800

Hence, this compound is a very effective sunscreen agent which is active in the UV-B range.

It should be appreciated that the intermediate compound obtained prior to carrying out the last step in the sequence of the process had the formula:

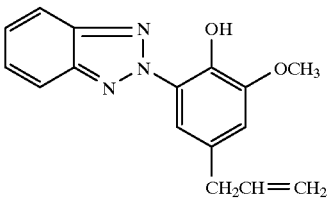

EXAMPLE 5

A specific formulation of a sunscreen cosmetic composition according to the invention, i.e, a sunscreen cream, is comprised of:

| | | |
|---|---|---|
| (i) | Compound of Example 1 | 5 g |
| (ii) | Mixture of cetyl/stearyl alcohol and oxyethylenated cetyl/stearyl alcohol containing 33 mols of EO ("SINNOVAX AO" marketed by HENKEL) | 7 g |
| (iii) | Non-self-emulsifying mixture of glycerol mono- and distearates | 2 g |
| (iv) | Cetyl alcohol | 1.5 g |
| (v) | Benzoate of $C_{12}$–$C_{15}$ alcohols ("FINSOLV TN" marketed by WITCO) | 20 g |
| (vi) | Polydimethylsiloxane | 1.5 g |
| (vii) | Glycerol | 17.5 g |
| (viii) | Perfume, preservative | qs |
| (ix) | Water | qs 100 g |

This cream was prepared according to the traditional techniques for preparing emulsions, by dissolving the sunscreen in the fatty phase containing the emulsifiers, heating this fatty phase to about 70°–80° C. and adding the water, heated to the same temperature, with brisk stirring. The stirring was maintained for 10 to 15 minutes, the mixture was then permitted to cool with moderate stirring and, at about 40° C., the perfume and preservative were lastly added.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising a photoprotecting effective amount of a compound having one of the formulae (1) to (3):

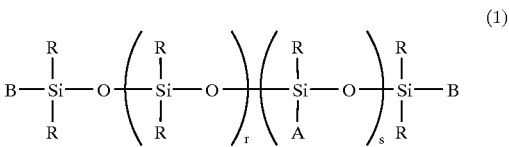

(1)

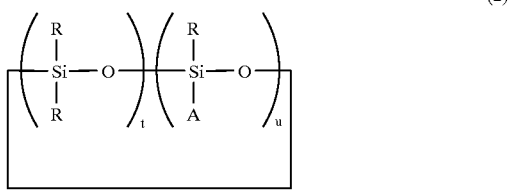

(2)

(3)

A—Si(R')$_3$ in which the radicals R, which may be identical or different, are each $C_1$–$C_{10}$ alkyl, phenyl or 3,3,3-trifluoropropyl radicals, at least 80% by number of the radicals R being methyl radicals; the radicals B, which may be identical or different, are each a radical R or a radical A as defined below; the radicals R', which may be identical or different, are each a $C_1$–$C_8$ alkyl radical or a phenyl radical; r is an integer ranging from 0 to 50, inclusive, and s is an integer ranging from 0 to 20, inclusive, with the proviso that, if s is zero, then at least one of the two radicals B is a radical A; u is an integer ranging from 1 to 6, inclusive, and t is in integer ranging from 0 to 10 inclusive, with the proviso that t+u is equal to or greater than 3; and the radical A is a univalent radical bonded directly to a silicon atom, and which has the following formula (4):

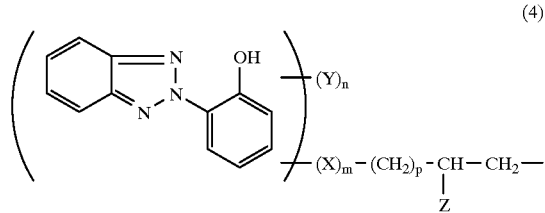

(4)

wherein the radicals Y, which may be identical or different, are each a $C_1$–$C_8$ alkyl radical, a halogen atom or a $C_1$–$C_4$ alkoxy radical, with the proviso that, in the latter event, two adjacent radicals Y on the same aromatic nucleus can together form an alkylidenedioxy radical in which the alkylidene group has from 1 to 2 carbons atoms; X is O or NH; Z is hydrogen or a $C_1$–$C_4$ alkyl radical; n is an integer ranging from 0 to 3, inclusive; m is 0 or 1, with the proviso that when m is zero, or when m is equal to 1 and X is NH, necessarily (i) n cannot be zero and (ii) at least one of the radicals Y is an alkoxy radical; and p is an integer ranging from 1 to 10, inclusive, in a cosmetically acceptable vehicle, carrier or diluent therefor.

2. The sunscreen/cosmetic composition as defined by claim 1, said cosmetically acceptable vehicle, carrier or diluent comprising at least one fatty phase or at least one organic solvent.

3. The sunscreen/cosmetic composition as defined by claim 1, comprising an oil-in-water or water-in-oil emulsion.

4. The sunscreen/cosmetic composition as defined by claim 1, comprising from 0.1% to 20% by weight of said photoprotecting compound.

5. A method for protecting human skin and/or hair against the deleterious effects of ultraviolet irradiation, comprising topically applying thereto an effective amount of the sunscreen/cosmetic composition as defined by claim 1.

6. A method for protecting human skin and/or hair against the deleterious effects of solar radiation, comprising topically applying thereto an effective amount of the sunscreen/cosmetic composition as defined by claim 1.

* * * * *